United States Patent
Hielscher et al.

(10) Patent No.: US 10,376,150 B2
(45) Date of Patent: Aug. 13, 2019

(54) INTERFACING SYSTEMS, DEVICES, AND METHODS FOR OPTICAL IMAGING

(71) Applicant: The Trustees of Columbia University in the City of New York, New York, NY (US)

(72) Inventors: Andreas H. Hielscher, Brooklyn, NY (US); Molly L. Flexman, New York, NY (US); Keith Yeager, Jersey City, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 14/348,072

(22) PCT Filed: Sep. 28, 2012

(86) PCT No.: PCT/US2012/058004
§ 371 (c)(1),
(2) Date: Mar. 28, 2014

(87) PCT Pub. No.: WO2013/049629
PCT Pub. Date: Apr. 4, 2013

(65) Prior Publication Data
US 2014/0236003 A1 Aug. 21, 2014

Related U.S. Application Data

(60) Provisional application No. 61/541,503, filed on Sep. 30, 2011.

(51) Int. Cl.
*A61B 5/05* (2006.01)
*A61B 5/00* (2006.01)

(52) U.S. Cl.
CPC .......... *A61B 5/0091* (2013.01); *A61B 5/0064* (2013.01); *A61B 5/708* (2013.01); *A61B 5/4312* (2013.01); *A61B 2562/146* (2013.01)

(58) Field of Classification Search
CPC .................................................. A61B 5/0064
See application file for complete search history.

(56) References Cited

U.S. PATENT DOCUMENTS 6,081,322 A * 6/2000 Barbour ............. G01N 21/4795
356/337
7,332,722 B1 * 2/2008 Tran ....................... A61B 6/037
250/363.09

(Continued)

FOREIGN PATENT DOCUMENTS

JP     3000858 U    6/1994
JP     H6-44510 U   6/1994

(Continued)

OTHER PUBLICATIONS

McBride et al., "Spectroscopic diffuse optical tomography for the quantitative assessment of hemoglobin concentration and oxygen saturation in breast tissue," Sep. 1, 1999, Applied Optics, vol. 38, No. 25, pp. 5480-5490.*

(Continued)

*Primary Examiner* — Jonathan Cwern
(74) *Attorney, Agent, or Firm* — Potomac Law Group, PLLC; Mark Catan

(57) ABSTRACT

An imaging interface for diffuse optical tomography of breast includes a plurality of concentric rings. Each concentric ring can include a plurality of optical input/output apertures arranged on a radially inner surface thereof. The rings can have different inner and outer diameters from each other and can be arranged in a stacked configuration. The rings can translate independently of each other along a central axis of the stack. During imaging the breast is (Continued)

inserted into an inner region of the stacked rings. The rings can be translated such that the optical input/output apertures are brought into touch contact (i.e., non-compressing contact) with the surface of the breast, so as to accommodate different size breasts. The rings may be translated such that the spacing between adjacent rings is increased for large breasts and reduced for smaller breasts. Rings may be removed or additional rings added to further accommodate additional breast sizes.

22 Claims, 8 Drawing Sheets

(56) References Cited

U.S. PATENT DOCUMENTS

| | | | | |
|---|---|---|---|---|
| 2002/0148966 | A1* | 10/2002 | Juni | A61B 6/037 250/363.04 |
| 2004/0039285 | A1* | 2/2004 | Ustuner | A61B 8/0825 600/459 |
| 2004/0087861 | A1* | 5/2004 | Jiang | A61B 5/0059 600/473 |
| 2005/0197583 | A1* | 9/2005 | Chance | A61B 5/0073 600/476 |
| 2007/0045547 | A1 | 3/2007 | Tumer | |
| 2008/0137806 | A1 | 6/2008 | Chang | |
| 2009/0005692 | A1* | 1/2009 | Intes | A61B 5/4312 600/477 |
| 2010/0274161 | A1 | 10/2010 | Azhari | |
| 2010/0292569 | A1* | 11/2010 | Hielscher | A61B 5/0073 600/425 |

FOREIGN PATENT DOCUMENTS

| | | |
|---|---|---|
| JP | H8-184593 A | 7/1996 |
| JP | H11-230090 A | 8/1999 |
| JP | 2001-521147 A | 11/2001 |
| WO | 1997031573 A1 | 9/1997 |
| WO | 1998023206 A1 | 6/1998 |
| WO | 1999027343 A2 | 6/1999 |
| WO | 2000006016 A1 | 2/2000 |
| WO | 2004014221 A2 | 2/2004 |
| WO | 2009033035 A1 | 3/2009 |
| WO | 2009077931 A1 | 6/2009 |
| WO | WO 2009114852 A2 * | 9/2009 ........... A61B 5/0073 |
| WO | WO 2012/065140 A2 | 5/2012 |

OTHER PUBLICATIONS

Nielsen et al., "Linear image reconstruction for a diffuse optical mammography system in a noncompressed geometry using scattering fluid," Oct. 21, 2008, Applied Optics, vol. 48, No. 10, pp. D1-D13.*
International Search Report and Written Opinion for International Application No. PCT/US2012/058004.
Klose et al., Investigations of RA-Diagnostics applying Optical Tomography in frequency-domain. SPIE vol. 3196, 1998.
Brooksby et al., "Imaging breast adipose and fibroglandular tissue molecular signatures by using hybrid MRI-guided near-infrared spectral tomography," PNAS, vol. 103, No. 23, Jan. 1, 2006, pp. 8828-8833.
Iftimia et al., "A compact, parallel-detection diffuse optical mammography system," Review of Scientific Instruments, vol. 74, No. 5, May 1, 2003, pp. 2836-2842.

Flexman et al., "Development of a dynamic optical tomographic breast imaging system with digital detection techniques," Proc. of SPIE, Feb. 12, 2009, vol. 7174, pp. 71740N-71740N-8. http://proceedings.spiedigitallibrary.org.
Schmitz et al., "Instrumental and calibration protocol for imaging dynamic features in dense-scattering media by optical tomography," Applied Optics, vol. 39, No. 34, Dec. 1, 2000, pp. 6466-6486. Retrieved from the Internet: URL:http://www.opticsinfobase.org/DirectPDFAccess/80BB4AF3-BDB9-137E-CD83A10B1F1E50D9_64747.pdf?da=1&id=64747&seq=0.
Supplementary European Search Report dated Feb. 26, 2015, in corresponding European Application No. EP 12 83 7252.
Office Action for Japanese Patent Application No. 2014-533418 dated Jul. 19, 2016 (includes English language translation).
Carp et al., "Dynamic functional and mechanical response of breast tissue to compression," Optics Express, Sep. 29, 2008, vol. 16(20), pp. 16064-16078.
Choe et al., "Differentiation of benign and malignant breast tumors by in-vivo three-dimensional parallel-plate diffuse optical tomography," Journal of Biomedical Optics, Mar./Apr. 2009, vol. 14(2), pp. 024020-1-024020-18.
Flexman et al., "Digital optical tomography system for dynamic breast imaging," Journal of Biomedical Optics, Jul. 1, 2011, vol. 16(7), pp. 076014-1-076014-16.
Hebden et al., "Optical tomography of the breast using a 32-channel time-resolved imager," Biomedical Topical Meeting 2002, Miami Beach, Florida, Apr. 7-10, 2002, Optical Society of America, pp. 187-189.
Office Action for European Patent Application No. 12837252.1 dated Dec. 7, 2017.
Schmitz et al., "Design and implementation of dynamic near-infrared optical tomographic imaging instrumentation for simultaneous dual-breast measurements," Applied Optics, Apr. 10, 2005, vol. 44(11), pp. 2140-2153.
Soliman et al., "Functional imaging using diffuse optical spectroscopy of neoadjuvant chemotherapy response in women with locally advanced breast cancer," Clinical Cancer Research, May 1, 2010, vol. 16(9), pp. 2605-2614.
Taroni et al., "Time-resolved optical mammography between 637 and 985 nm: clinical study on the detection and identification of breast lesions," Physics in Medicine and Biology, May 18, 2005, vol. 50(11), pp. 2469-2488.
Tornai et al., "A 3D gantry single photon emission tomograph with hemispherical coverage for dedicated breast imaging," Nuclear Instruments and Methods in Physics Research Section A, Jan. 21, 2003, vol. 497(1), pp. 157-167.
Tromberg et al., "Assessing the future of diffuse optical imaging technologies for breast cancer management," Medical Physics, Jun. 1, 2008, vol. 35(6), pp. 2443-2451.
Van De Ven et al., "Diffuse optical tomography of the breast: preliminary findings of a new prototype and comparison with magnetic resonance imaging," European Radiology, May 1, 2009, vol. 19(5), pp. 1108-1113.
Wang et al., "In vivo quantitative imaging of normal and cancerous breast tissue using broadband diffuse optical tomography," Medical Physics, Jul. 1, 2010, vol. 37(7), pp. 3715-3724.
Yates et al., "Optical tomography of the breast using a multi-channel time-resolved imager," Physics in Medicine and Biology, May 18, 2005, vol. 50(11), pp. 2503-2517.
Zhang et al., "Coregistered tomographic x-ray and optical breast imaging: initial results", Journal of Biomedical Optics, Mar./Apr. 2005, vol. 10(2), pp. 024033-1-024033-9.

* cited by examiner

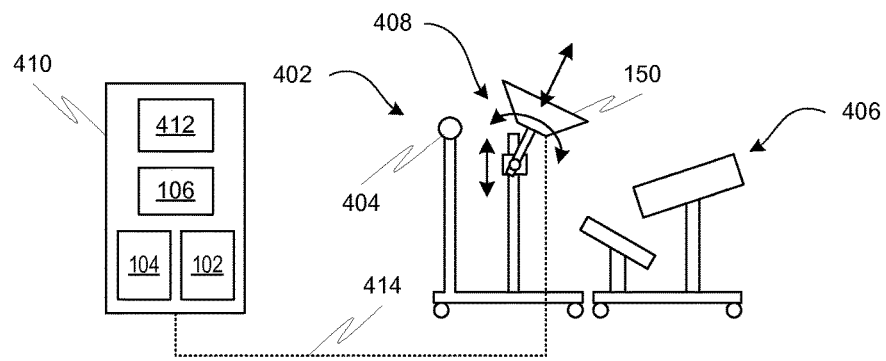
FIG. 4
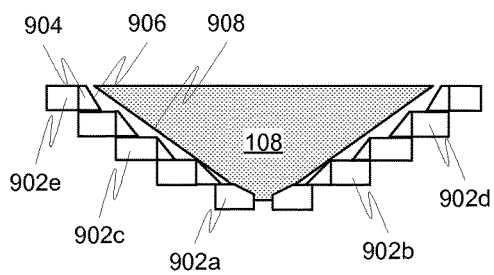      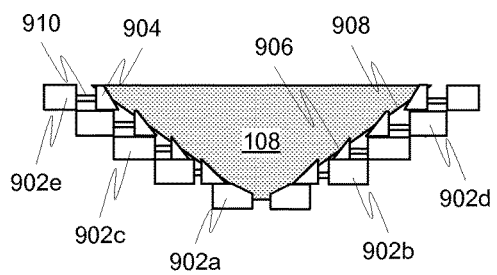
FIG. 9A              FIG. 9B
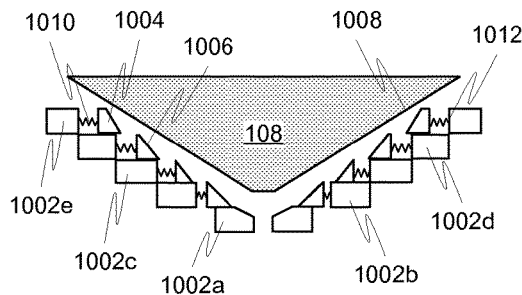      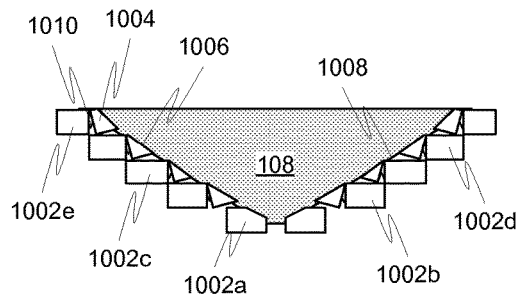
FIG. 10A             FIG. 10B
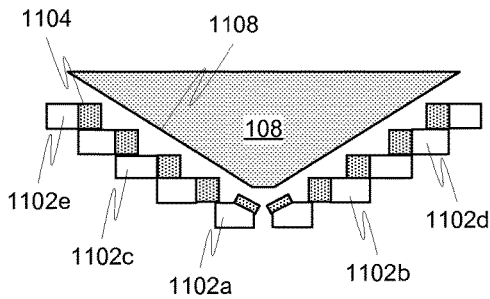      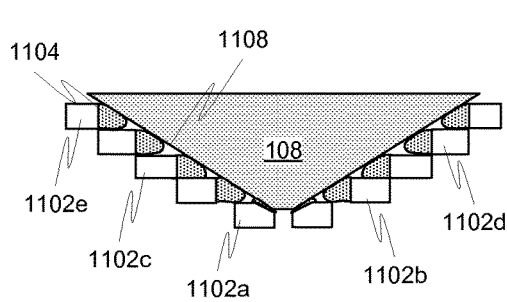
FIG. 11A             FIG. 11B

| Adjust Optical Switch and Update Gain Settings for: | Illuminate Sample With: | Convert Sample: | Send Data for ADC Channels: | mDSP | sDSP1 | sDSP2 | sDSP3 | DSPs Demodulate & Send Data to PC for: |
|---|---|---|---|---|---|---|---|---|
| SRC1, WL1&2 | | | | | | | | |
| | | Sample 1 | Channel 1&3 | ADC1&2 | ADC9&10 | ADC17&18 | ADC25&26 | |
| | | | | ADC3&4 | ADC11&12 | ADC19&20 | ADC27&28 | |
| | | | | ADC5&6 | ADC13&14 | ADC21&22 | ADC29&30 | |
| | | | | ADC7&8 | ADC15&16 | ADC23&24 | ADC31&32 | |
| | SRC1, WL1&2 | Sample 1 | Channel 2&4 | ADC1&2 | ADC9&10 | ADC17&18 | ADC25&26 | |
| | | | | ADC3&4 | ADC11&12 | ADC19&20 | ADC27&28 | |
| | | | | ADC5&6 | ADC13&14 | ADC21&22 | ADC29&30 | |
| | | | | ADC7&8 | ADC15&16 | ADC23&24 | ADC31&32 | |
| | | Sample 2 | Channel 2&4 | ADC1&2 | ADC9&10 | ADC17&18 | ADC25&26 | |
| | | ... | ... | ... | ... | ... | ... | |
| | | Sample 150 | Channel 2&4 | ADC7&8 | ADC15&16 | ADC23&24 | ADC31&32 | |
| SRC1, WL3&4 | | | | | | | | SRC1, WL1&2 |
| | SRC1, WL3&4 | Sample 1 | Channel 1&3 | ADC1&2 | ADC9&10 | ADC17&18 | ADC25&26 | |
| | | ... | ... | ... | ... | ... | ... | |
| | | Sample 150 | Channel 2&4 | ADC7&8 | ADC15&16 | ADC23&24 | ADC31&32 | |
| SRC2, WL1&2 | | | | | | | | SRC1, WL3&4 |
| | SRC2, WL1&2 | Sample 1 | Channel 1&3 | ADC1&2 | ADC9&10 | ADC17&18 | ADC25&26 | |
| | | ... | ... | ... | ... | ... | ... | |
| | | Sample 150 | Channel 2&4 | ADC7&8 | ADC15&16 | ADC23&24 | ADC31&32 | |
| ... | ... | ... | ... | ... | ... | ... | ... | ... |
| SRC32, WL3&4 | | | | | | | | |
| | SRC 32, WL3&4 | Sample 1 | Channel 1&3 | ADC1&2 | ADC9&10 | ADC17&18 | ADC25&26 | |
| | | ... | ... | ... | ... | ... | ... | |
| | | Sample 150 | Channel 2&4 | ADC7&8 | ADC15&16 | ADC23&24 | ADC31&32 | |
| | | | | | | | | SRC32, WL3&4 |

FIG. 7

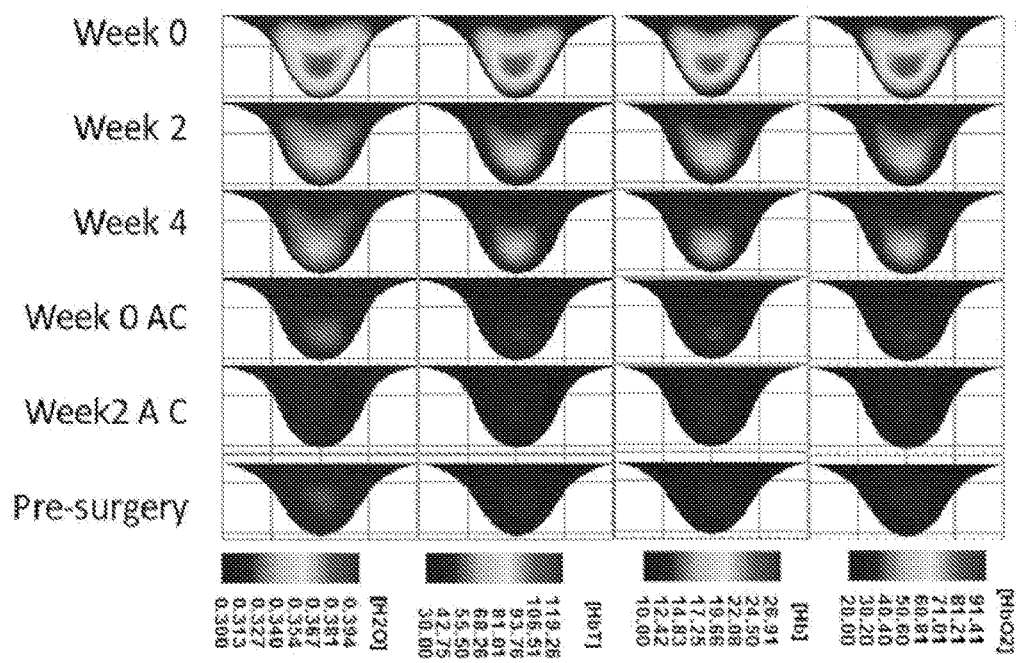
FIG. 8
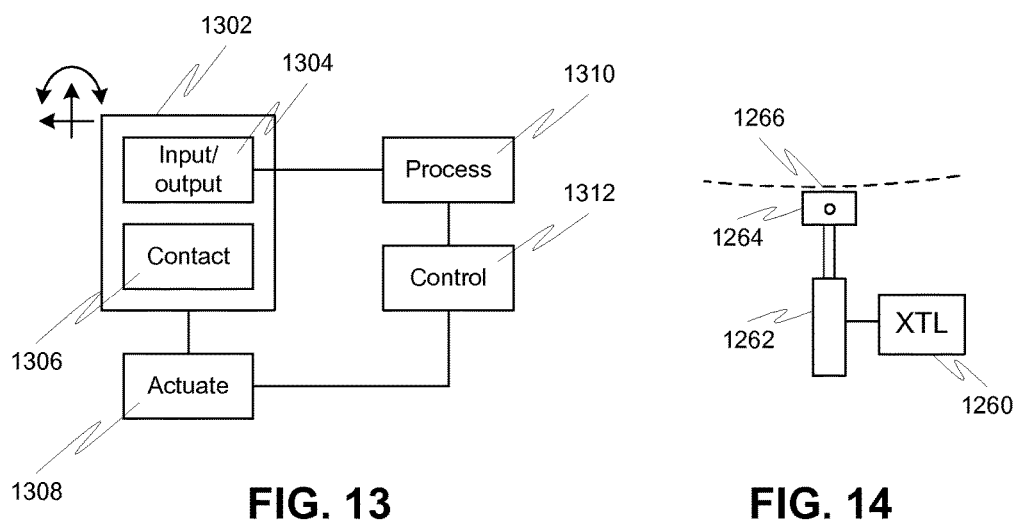
FIG. 13  FIG. 14

INTERFACING SYSTEMS, DEVICES, AND METHODS FOR OPTICAL IMAGING

CROSS-REFERENCE TO RELATED APPLICATIONS

The present application is a U.S. national stage filing under 35 U.S.C. § 371 of International Application No. PCT/US2012/058004 filed Sep. 28, 2012, which claims the benefit of U.S. Provisional Application No. 61/541,503, filed Sep. 30, 2011, all of which are hereby incorporated by reference herein in their entireties.

FIELD

The present disclosure relates generally to optical imaging of tissue, and, more particularly, to interfaces for diffuse optical imaging of breast tissue.

BACKGROUND

Breast cancer affects approximately 1 in 8 women in the United States and the incidence of breast cancer throughout the world is increasing. Breast cancer currently accounts for 28% of all new cancers diagnosed in women, with almost 40,000 deaths caused by breast cancer each year. The most commonly applied modality for breast cancer screening is X-ray mammography. However, its use of ionizing radiation limits the frequency with which this modality can be employed. Furthermore, mammography has been shown to be less reliable for young women and further, it causes patient discomfort. In addition, mammography suffers from a relatively high false positive rate. Magnetic resonance imaging (MRI) is a powerful tool to monitor women at a high-risk for breast cancer, but its high cost and variable specificity hinders its use as a general screening modality. Ultrasound imaging can be used as a second-line diagnostic tool to differentiate masses detected by X-ray mammography, but operator variability and low specificity make it unsuitable for front-line screening.

SUMMARY

Diffuse optical tomography (DOT) uses low-intensity light in the near-infrared to infrared wavelength range to probe and characterize breast tissue. Its use of non-ionizing radiation and the low cost of this imaging modality make it potentially ideal for breast cancer screening. In addition, DOT derives contrast from physiological changes in tissue which can be used to detect and characterize cancerous lesions. For example, growing tumors require increased vascularization to continue to receive adequate blood supply and the vasculature formed by tumors tends to be much more chaotic and leakier than vasculature in normal tissue. These physiological changes result in measurable changes in chromophore composition and density and thus in the behavior of light passing through the tumor tissue as compared to the surrounding tissue. By using multiple wavelengths of light, it is possible to extract the concentrations of the primary light absorbers in the breast including oxygenated and deoxygenated hemoglobin, lipid and water. Furthermore, light is also sensitive to scattering changes in tissue. Differences in the scattering properties of tissue, e.g., due to cellular changes such as enlarged and denser nuclei, can be used to detect breast cancer. Specifically, increases in scattering power and scattering amplitude can differentiate certain types of cancer from healthy tissue.

DOT involves illuminating the breast with light in the red to near-infrared wavelength range and then detecting the transmitted and reflected light through the breast. Using multiple wavelengths it is possible to create 3-D maps of the blood, fat, water, and collagen content of the breast. Breast interfaces are responsible for bringing the illuminating light into contact with the breast, and then bringing the detected light from the breast to the photo-detector. In order to create full 3-D images of the entire breast, the interface is constructed such that the optical sources can deliver light to the entire breast and the detectors can collect light from the entire breast. In addition, the interface allows complete coverage of the breast, thereby allowing full probing of the breast tissue to detection of tumors that may be lie anywhere between the retro-areolar region to close to the chest wall. Moreover, the disclosed interface can accommodate a variety of breast sizes while maintaining contact of the optical inputs/outputs with the breast surface with minimal to no compression of the breast, thereby providing a clinically useful design that minimizes or at least reduces patient discomfort and the need for optical matching fluids.

In embodiments, the breast imaging interface includes a plurality of concentric rings that include a plurality of optical input/output apertures arranged on a radially inner surface thereof. The rings have respective inner and outer diameters that differ from each other and are arranged in stacked configuration to define a progressive anatomically-accommodating discontinuous internal surface by stacking in order of increasing diameter. The rings can translate independently of each other along a central axis of the stack. During imaging the breast is inserted into an inner region formed by the radially inner surfaces of the stacked rings. The rings can be translated such that the optical input/output apertures are brought close to, or preferably into direct contact (i.e., non-compressing contact) with, the surface of the breast. The adjustability allows the structure to accommodate different size breasts. For example, the rings may be translated such that the spacing between adjacent rings is increased for large breasts and reduced for smaller breasts. Rings may be removed or additional rings added to further accommodate additional breast sizes and shapes. The ring interface can include additional features that ensure direct contact between the optical input/outputs of the rings and the surface of the breast while minimizing breast compression.

In embodiments, an interface device for optical tomographic imaging of a body part can include optical emitters and receivers supported on annular members that are interattachable. The optical emitters and receivers can each face at least partly toward an axis of a respective one of the annular members. The annular members can have a range of sizes and be configured to be interattached such that the optical emitters and receivers are distributed over a concave bounding surface shaped to receive a predefined body part. Ones of the annular members can be selected responsively to the size and/or shape of a target body part of a particular person. The selected ones of the annular members can then be interattached and positioned axially to conform to the size and/or shape. Optical tomographic data can be generated using the optical emitters and receivers.

In embodiments, an interfacing device for optical tomographic imaging of breast tissue, includes a plurality of annular members. The plurality of annular members can be concentrically arranged in a stacked configuration along an axial direction. Each of the annular members can have a minimum inner diameter that is different from that of the other annular members. The annular members can be arranged such that the inner diameters increase from a first axial end of the stack to an opposite second axial end of the stack. At least some of the annular members possess one or more optical input apertures and optical output apertures arranged on an inner surface thereof. The stack can form an inner boundary surface defined by the annular members for receiving the breast tissue for imaging. The annular members can be supported for translation with respect to each other along the axial direction so as to adjust the spacing between adjacent annular members in said stack, thereby permitting the adjustment of the depth and shape of the inner bounding surface. The translation amount of each annular member can be quantified, for example, by a respective displacement sensor for use in image reconstruction and/or reproducibility in subsequent imaging sessions. Each annular member can be translated by a respective translation device, such as a stepper motor, linear actuator, or other translation device.

In embodiments, a system for optical tomographic imaging of breast tissue includes a translating ring interface, a plurality of illumination sources, a plurality of first optical fibers, a plurality of detectors, a plurality of second optical fibers, and a processor. The translating ring interface includes a plurality of annular members concentrically arranged in a stacked configuration along an axial direction. The annular members can be arranged with inner diameters that increase progressively from a first axial end of the stack to a second opposite axial end of the stack. Each of the annular members can have a plurality of optical input apertures and optical output apertures arranged on an inner surface thereof. The interface can have an inner region bounded by the inner surfaces of the annular members for receiving the breast tissue during imaging. The illumination sources can be substantially monochromatic. The plurality of first optical fibers may connect the plurality of illumination sources to the optical input apertures. The plurality of second optical fibers can connect the plurality of detectors to the optical output apertures. The processor can be configured to control the illumination sources to illuminate the breast tissue with light via one of the first optical fibers and to control the detectors to detect light from the breast tissue via the second optical fibers. The processor can also be configured to modulate the amplitude of light from the illumination sources during illumination and to demodulate the detected light to generate detected light signals.

In embodiments, a method for optical tomographic imaging of breast tissue can include inserting the breast tissue into an inner region of a translating ring interface. The translating ring interface can include a plurality of annular members concentrically arranged in a stacked configuration along an axial direction. The annular members can be arranged with inner diameters that increase from a first axial end of the stack to an opposite axial end of the stack. Each of the annular members can include a plurality of apertures arranged on an inner surface thereof. The inner region can be bounded by the inner surfaces of the annular members. The method can further include translating the annular members along the axial direction such that the respective inner surface is in touch contact with a surface of the breast tissue. The method can also include illuminating the breast tissue with light via one of the apertures and receiving light from the breast tissue via others of the apertures so as to generate detected light signals. The method can include reconstructing an image of the breast tissue based on the detected light signals.

In embodiments, an interfacing device for optical tomographic imaging of breast tissue can include a plurality of annular members concentrically arranged in a stacked configuration along an axial direction. The annular members can include radially inner portions with optical input apertures and optical output apertures arranged on inner surfaces thereof. The stack can form an inner region bounded by the inner surfaces of the radially inner portions for receiving the breast tissue for imaging. The annular members can be constructed to be translated with respect to each other along the axial direction so as to adjust the spacing between adjacent annular members in said stack. The radially inner portions for each annular member can be constructed such that the respective inner surfaces can be displaced in a radial direction of the annular member to accommodate different sizes of breast tissue. In addition, each member can be positioned independent of the other annular members, for example, in an axial direction as well as rotationally out of a plane perpendicular to the axial direction so as to accommodate a wide range of body types and sizes using a single imaging interface.

In embodiments, a structure can interface a body part of a patient with a plurality of optical fibers carrying illuminating light from a light source to the body part and with a plurality of optical fibers carrying detected light from the body part to a light detector so as to effect diffuse optical tomography. The structure can include a first set of a plurality of ring-like elements of increasing diameters positioned one on top of the other with the ring-like element having the smallest diameter at the bottom. The ring-like elements together form a cup-shaped structure configured to hold the body part therein. Each ring-like element can be detachably attached to an adjacent ring-like element and can have an adjustable height along a vertical direction. The number of ring-like elements and the heights of the ring-like elements can be adjustable based on the size and shape of the body part. Each ring-like element can have a plurality of optical fibers connected thereto. A system for interfacing a body part of a patient with the plurality of optical fibers can include the structure and a holding device for holding the first and second sets of ring-like elements adjacent to each other such that each set holds a corresponding breast. The distance between the first and second sets can be adjustable to correspond to the distance between the breasts.

In embodiments, a structure can interface a body part of a patient with a plurality of optical fibers carrying illuminating light from a light source to the body part and a mechanism effective to detected light received from the body part at multiple locations at the surface of the body part so as to effect diffuse optical tomography. The structure can include a chassis defining a body part-conforming structure configured to hold the body part therein. The chassis can support multiple optical fiber light-receiving portions which are movable relative to each other on the chassis to allow a body conforming shape to be changed and to permit a body part to be inserted in a recess defined thereby. The structure can further include a system to which the optical fibers are attached at an end opposite the light-receiving portions to detect and process light signals and generate an optical tomographic image and display the same.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIG. 4 illustrates a setup for breast screening employing a translating ring interface, according to one or more embodiments of the disclosed subject matter.

FIG. 7 illustrates the timing sequences of synchronization between components of the DOT system, according to one or more embodiments of the disclosed subject matter.

FIG. 8 are DOT images of a tumor-bearing breast obtained using the breast screening setup of FIGS. 5A-5C.

FIGS. 9A-9B illustrate operation of a translating ring interface with extensible portions for contact with the breast during imaging, according to one or more embodiments of the disclosed subject matter.

FIGS. 10A-10B illustrate operation of a translating ring interface with spring-actuated portions for contact with the breast during imaging, according to one or more embodiments of the disclosed subject matter.

FIGS. 11A-11B illustrate operation of a translating ring interface with deformable portions for contact with the breast during imaging, according to one or more embodiments of the disclosed subject matter.

FIG. 13 is a schematic diagram of an interface for conformal contact imaging of a body part, according to one or more embodiments of the disclosed subject matter.

FIG. 14 is a diagram of an actuator component that may be used for implementation of the embodiment of FIG. 13 and other embodiments.

DETAILED DESCRIPTION

Diffuse optical tomography uses endogenous contrast generated by the physiology of targeted tissue structures, either in steady state or after perturbing the state of the physiology in order to generate a transient response to differentiate between healthy and cancerous tissue. Due to excess endothelial cells and abnormal perivascular cells, tumor vasculature is disorganized and hyper-permeable. The leakiness of the vessels makes them unable to maintain a pressure gradient between the vessels and the interstitial space and also impairs the flow of fluid and molecules. In addition, tumor cells consume large amounts of oxygen which, coupled with poor oxygen delivery, leads to tumor hypoxia. Overall, these changes affect the hemodynamic response of the cancerous tissue, providing additional information about the tissue that can be used for diagnosis. Such sources of dynamic contrast to evoke a hemodynamic response can include, but are not limited to, a respiratory maneuver, the application of pressure to the breast, the respiration of carbogen, and the injection of indocyanine green (ICG).

In exploring dynamic changes, adequate temporal resolution is necessary to capture the transient responses. In addition, a large number of source and detector positions are required to cover the breast for adequate 3-D spatial resolution. Further, imaging both breasts simultaneously allows for the contra-lateral breast to serve as a reference that is under the same external stimulus as the tumor-bearing breast. To accomplish these imaging goals, imaging systems according to embodiments of the disclosed subject matter are able to acquire large amounts of data at fast imaging speeds. In addition, the imaging systems according to embodiments of the disclosed subject matter provide a large dynamic range to capture the varying amplitudes of reflected and transmitted light, thereby accommodating the large variety of geometries involved in breast optical tomography.

According to embodiments of the disclosed subject matter, an optical tomographic breast imaging system for dynamic optical breast imaging employs multiple digital signal processing (DSP) chips arranged in a master-slave setup to maximize the processing throughput, reduce noise, and provide a system design that can be scaled to accommodate a variable number of detectors and wavelengths. The system can image both breasts simultaneous, for example, at 1.7 Hz using four wavelengths and sixty-four sources and one-hundred twenty-eight detectors with a large dynamic range (e.g., approximately $10^8$).

Figure 1:
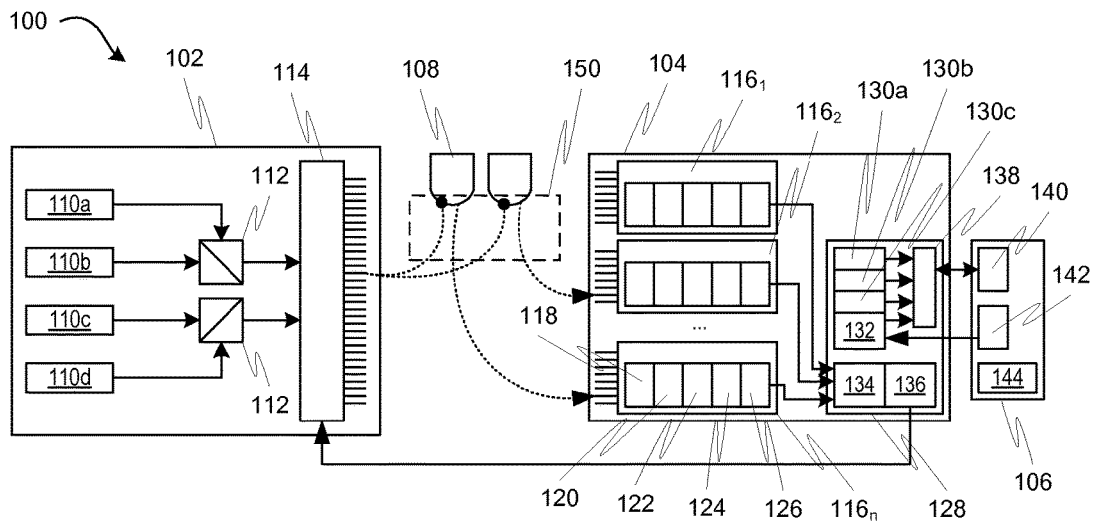
FIG. 1 is a schematic diagram showing the components of a diffuse optical tomography (DOT) system for breast imaging, according to one or more embodiments of the disclosed subject matter.

Referring to FIG. 1, an optical tomography system 100 includes a light input unit 102 for generating illumination light (e.g., substantially monochromatic light), a detection unit 104 for measuring and quantifying the light from the target tissue 108, and a terminal 106. Terminal 106 can include a user interface unit 144 (e.g., a graphical user interface) and/or a host computer to allow an operator to control and view the results of the imaging. The input unit 102 generates light with which the target 108 is illuminated via one or more optical fibers. The system 100 uses a plurality of illumination sources 110a-110d, each of which can generate a separate wavelength for illuminating the sample 108, either simultaneously with or after illumination with other wavelengths. For example, four wavelengths of near-infrared light at 765 nm, 808 nm, 827 nm, and 905 nm generated by continuous-wave high power laser diodes.

Each laser diode 110a-110d can be controlled by a laser driver controller and modulated with an input current at either 5 kHz (e.g., for wavelengths of 765 nm and 808 mm) or 7 kHz (e.g., for wavelengths of 827 nm and 905 nm). Modulating the laser light intensity allows for simultaneous illumination of the target with multiple wavelengths as well as the rejection of ambient light. Other modulation frequencies are also possible so long as the frequencies are chosen to allow sufficient discrimination of the detected light during demodulation. The four wavelengths from light sources 110a-110d are passed through two wave division multiplexers 112 to create two separate streams of light. For example, a first stream may be created using light from source 110a (e.g., at a wavelength of 765 nm modulated at 5 kHz) and light from source 110b (e.g., at a wavelength of 827 nm modulated at 7 kHz) while a second stream may be created using light from source 110c (e.g., at a wavelength of 808 nm modulated at 5 kHz) and light from source 110d (e.g., at a wavelength of 905 nm modulated at 7 kHz).

Since each light stream is detected with the same hardware (i.e., detection unit 104), the same amount of gain is applied to all wavelengths of the stream. In cases where the attenuation through the tissue is significantly different at the various wavelengths it can be difficult to find one gain setting to accommodate all four wavelengths. The use of two different streams of light with two wavelength in each stream may address this issue. However, it also contemplated that the four wavelengths (or more) can be combined in a single stream using multiple modulation frequencies. The modulation frequency can be generated by a direct digital synthesis (DDS) chip and passed through a series of filters as well as offset and amplitude adjustment stages prior to being input to the laser driver controller. The output frequency of the DDS chip can be controlled by a programmable microcontroller.

The two light streams can be passed to an optical switch 114, for example, a 2×32 opto-mechanical switch. The switch 114 can illuminate the target 108 at one source position with the first wavelength set (e.g., 765 nm & 827 nm) and then the second wavelength set (e.g., 808 nm & 905 nm) before moving onto the next source position. The switching between different source illumination positions can continue until all source positions (i.e., the input apertures of the imaging interface 150 surrounding the target) have illuminated the target 108. The switching can be customizable so that the system 100 can employ two wavelengths twice as quickly since it doesn't need to repeat the measurements at each source position a second time for the additional wavelength set. The optical switch can take less than 7 ms to settle when switching between positions.

Multimode optical fibers (e.g., 65 μm inner diameter, 125 μm outer diameter) can leave the switch 114 and then bifurcate to simultaneously illuminate both the left and right breast 108. The fibers can be brought into touch contact (i.e., non-compressive contact) with the breast 108 using a translating ring interface 150, which is designed to accommodate various sizes and shapes of breasts 108. The translating ring interface 150 can also include multimode optical fibers for conveying light from the breast 108 during illumination to the detection unit 104 for demodulation and signal processing.

Figure 2A:
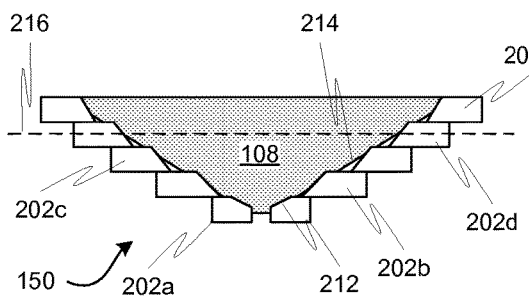
FIG. 2A illustrates use of a translating ring interface for imaging of a small size breast, according to one or more embodiments of the disclosed subject matter.
Figure 2B:
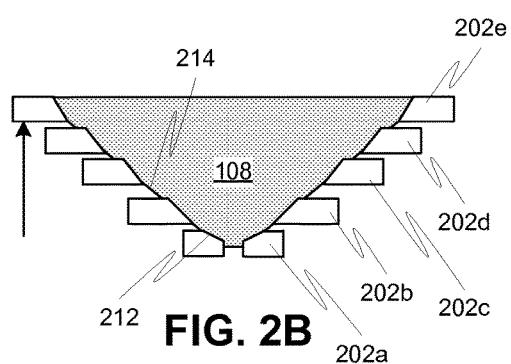
FIG. 2B illustrates use of a translating ring interface for imaging of a large size breast, according to one or more embodiments of the disclosed subject matter.

The translating ring interface 150 can include a plurality of annular shaped members 202a-202e stacked over each other as shown in FIGS. 2A-2B. The annular members may be of increasing diameter, such that the annular member 202a at the bottom of the stack has the smallest diameter while the annular member 202e at the top of the stack has the largest diameter. Each annular member 202 can include an inner surface 212 constructed to come into contact with a surface 214 of the breast 108. The stack of annular members 202a-202e thus form an inner region bounded by the inner surfaces 212 of each annular member for receiving the breast 108 for imaging.

In addition, the inner surface 212 includes a plurality of optical input and output apertures coupled to respective optical fibers for providing illuminating light to the breast 108 and directing light from the breast 108 to detectors, respectively. For example, the translating ring interface 150 can include four annular members of increasing diameters (e.g., 4 cm, 8 cm, 12 cm, and 16 cm). As the rings increase in size, more apertures for optical input/output may be provided. For example, the smallest ring may have eight apertures, the second smallest ring may have twelve apertures, the third smallest ring may have sixteen apertures, and the largest ring may have twenty eight apertures. Alternatively, the translating ring interface 150 can include five annular members of increasing diameters. For example, the smallest ring may have eight apertures, the second smallest ring may have twelve apertures, the middle ring may have twelve apertures, the next largest ring may have sixteen apertures, and the largest ring may have sixteen apertures.

With the exception of the smallest annular member (e.g., member 202a), each annular member 202 can be removed to accommodate various breast sizes from A (e.g., the smallest two members 202a, 202b are used) to DDD (e.g., all rings from 202a to 202e are used). The rings 202 can also independently translate in an axial direction of the stack, as shown in FIG. 2B. In particular, each annular member 202 is moved in the axial direction to a position along the breast 108 where the inner surface 212 is in touch contact with the surface 214 of the breast 108, i.e., where a diameter of the breast corresponds to a diameter of the inner surface 212. Additionally or alternatively, each annular member can be capable of rotational displacement out of a plane. For example, the annular member can be rotated out of plane 216, which is perpendicular to an axial direction of the interface 150, such that optical apertures on opposite portions of the annular member are at different height in the axial direction. Larger and/or differently shaped breasts 108 can thus be accommodated by appropriate translation of each annular member 202 to vary the spacing between annular members and arrange the inner surface 212 at the appropriate position along the breast.

This translation can be accomplished manually and secured by spring plungers that interact with shafts that have holes every 5 mm. Two or more shafts can attach to each ring and hold it in place. Alternatively, a translation device can be provided for independently moving each annular member 202 in the axial direction. For example, the translation device can be a stepper motor, a linear actuator, or any other translation device. The translation device may include position feedback or a position sensor for keeping track of the precise location of each annular member 202 and the apertures thereon for use in image reconstruction. The precise location of each interface and thereby each optical input/ output with respect to the body part being imaged can be used for appropriate generation of a reconstruction mesh for image formation. In addition, the precise location information as well as the ability to control the location of each annular member can allow for repeatable measurements across multiple time periods. The sources and/or detectors can thus be arranged in substantially the same position as a previous imaging session, which may be useful in clinical and/or therapeutic applications such as breast cancer detection and/or treatment.

Figure 2C:
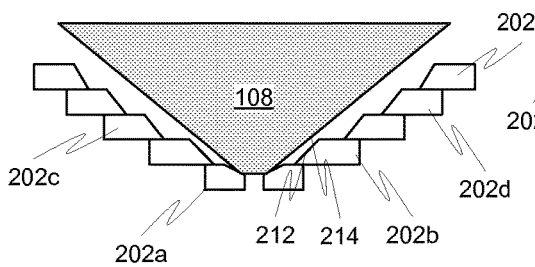
FIGS. 2C-2D illustrate actuation of a translating ring interface from an initial state to a touch contact state with a breast, according to one or more embodiments of the disclosed subject matter.
Figure 2D:
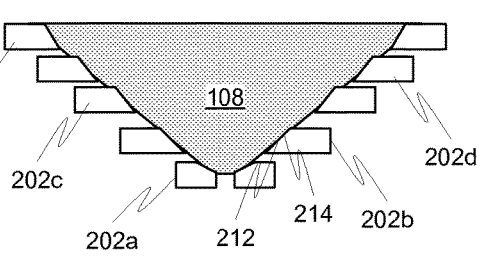

Referring to FIG. 2C, the breast imaging interface 150 is shown in an initial position for imaging of breast tissue 108. The breast 108 can be brought into contact with the first member 202a (e.g., the smallest annular member). The members 202b-202e can be initially arranged such that the respective surface 212 thereof is spaced from the breast surface 214. Each member 202b-202e can be separately actuated in an axial direction (and/or rotated out of plane) to bring the respective surface 212 into touch contact with the breast surface 214, as shown in FIG. 2D. Each member 202 can be positioned by an actuator (not shown). Displacement of the member 202 can be determined by appropriate mechanisms in order to precisely locate the optical inputs and outputs for image reconstruction. For example, displacement of the members can be determined based on sensors or encoders associated with the actuator.

Figure 2E:
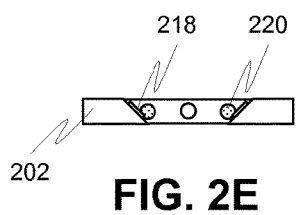
FIGS. 2E-2F illustrates a cross-sectional view and top view of a translating ring interface with a touch confirmation mechanism, according to one or more embodiments of the disclosed subject matter.
Figure 2F:
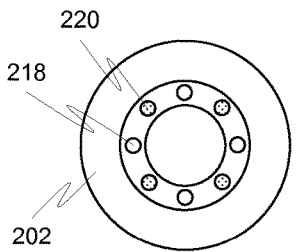
Figure 3A:
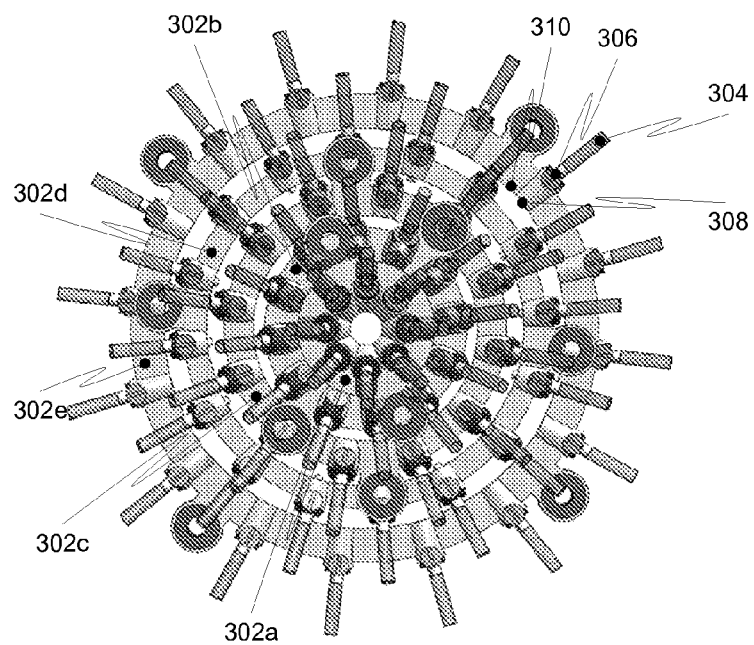
FIG. 3A is a top view rendering of a translating ring interface, according to one or more embodiments of the disclosed subject matter.
Figure 3B:
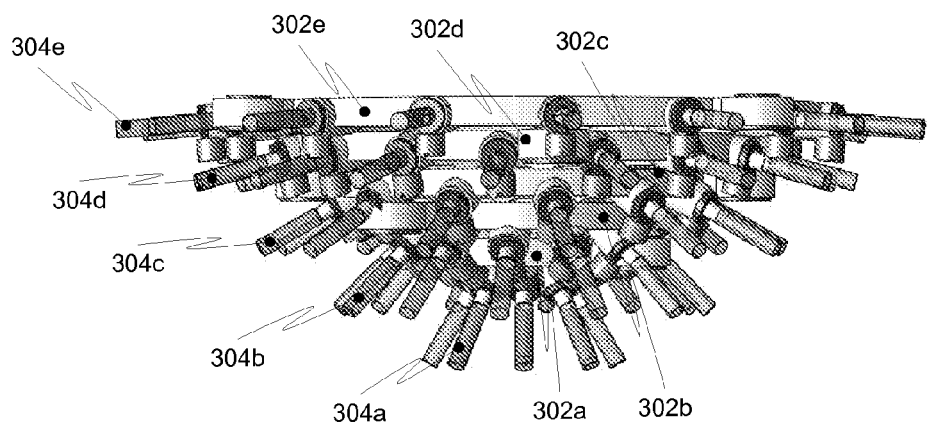
FIG. 3B is a side view rendering of the translating ring interface of FIG. 3A in a configuration for small size breast imaging, according to one or more embodiments of the disclosed subject matter.
Figure 3C:
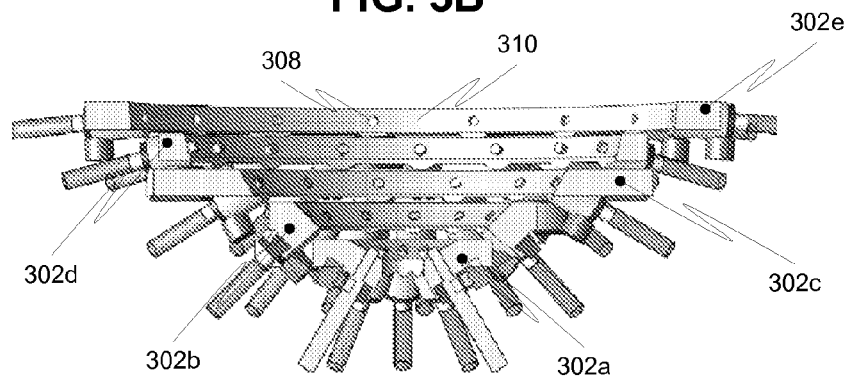
FIG. 3C is a cross-sectional view rendering of the translating ring interface of FIG. 3A in a configuration for small size breast imaging, according to one or more embodiments of the disclosed subject matter.
Figure 3D:
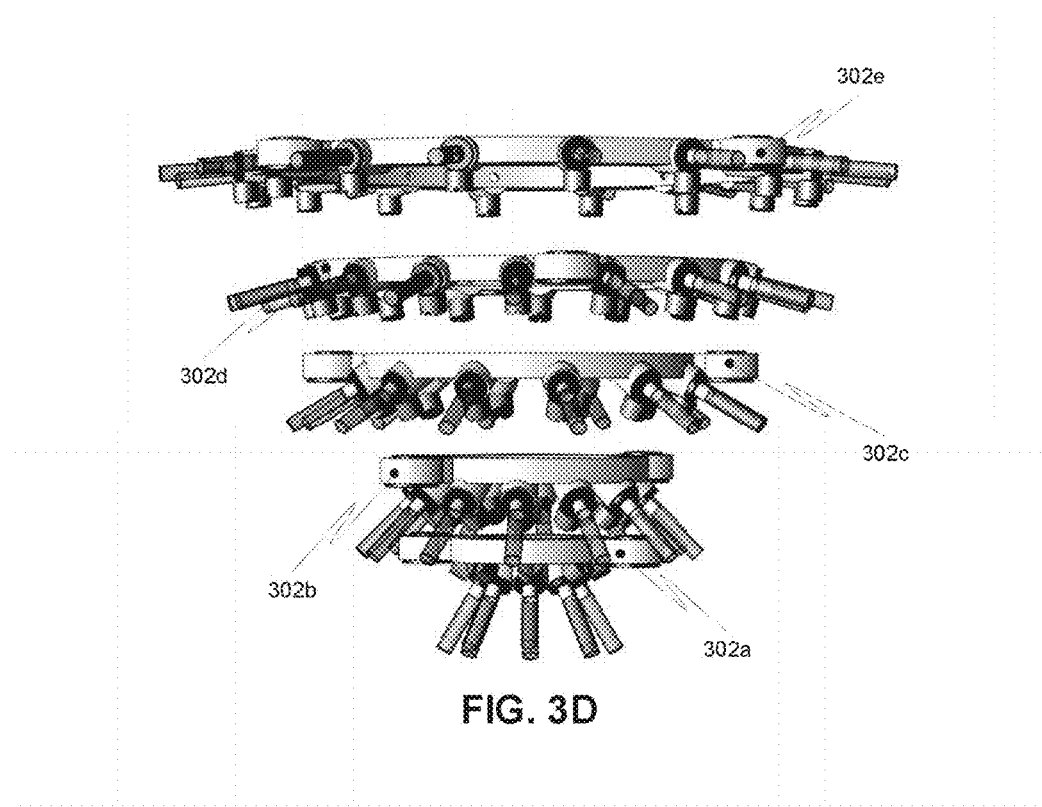
FIG. 3D is a side view rendering of the translating ring interface of FIG. 3A in a configuration for large size breast imaging, according to one or more embodiments of the disclosed subject matter.

One or more of the members 202 can be provided with one or more touch confirmation devices 220 in addition to the optical input/output apertures 218, as shown in FIGS. 2E-2F. For example, touch confirmation device 220 can be an optical sensor, conductivity sensor, acoustic sensor, or any other means for determining when/if the member surface 212 is in touch contact with the tissue to be imaged. A processor or other control device can coordinate actuation of each member 202 using signals from the touch confirmation devices 220 as feedback to bring the surface 212 into touch contact. Alternatively or additionally, the actuator may incorporate force feedback whereby an increase in the force required to displace the member 202 indicates contact with the tissue to be imaged. Alternatively or additionally, optical characteristics of the imaging system, for example, the gain required to read out specific optical signals via optical apertures 218 can used to provide feedback regarding touch contact, as described further below. Feedback control may be based on FIGS. 3A-3D show various configurations of an interfacing device according to one or more embodiments of the disclosed subject matter. FIG. 3A shows a top view of the interfacing device. FIGS. 3B-3C show a side view and cross-sectional view of the interfacing device in a small breast imaging configuration. FIG. 3D shows a side view of the interfacing device in a large breast imaging configuration.

As noted above, the interfacing device may include a plurality of annular members 302a-302e, each with an inner surface 310 for contacting a breast 108 during imaging. As shown in FIG. 3C, each inner surface 310 includes apertures 308 for directing light to and collecting light from the breast 108. Apertures 308 for directing light to the breast 108 (i.e., optical input apertures) can be alternately arranged with apertures for collecting light from the breast 108 (i.e., optical output apertures) around a circumference of the inner surface 310 of each annular member 302. For example, the optical input apertures and optical output apertures can be arranged equidistantly about the circumference of the inner surface. Optical fibers can be coupled to each aperture 308 by a shaft collar 304 that secures at 306 to the tip of the fiber.

The angle of the shaft collar 304 (and thus the fiber at the annular member) and/or the inner surface 310 can change based on the size of the annular member 302 so as to keep the input/output substantially normal to the breast tissue surface. For example, the shaft collar 304a of the smallest annular member 302a may be disposed at an angle closest to the axial direction of the interfacing device while the shaft collar 304e of the largest annular member 302e may be disposed at angle farther from the axial direction (e.g., almost perpendicular to the axial direction). The shaft collars 304 for the other annular members may vary between the extremes of the smallest member 302a and largest member 302e. For example, the angle of the shaft collar 304a of the smallest annular member 302a can be 60° with respect to the horizontal plane (i.e., or 30° with respect to the axial direction) and can decrease by approximately 15° for each subsequent annular member 302 in the stack (i.e., 45°, 30°, 15°, 0° with respect to the horizontal plane for shaft collars for members 302b-302e, respectively). Similarly, the inner surface 310 of the smallest annular member 302a can be disposed at angle closest to parallel with the horizontal plane while the inner surface 310 of the largest annular member 302e can be disposed at an angle closest to parallel with the axial direction, with the other annular members 302b-302d having inner surfaces at an angle between the two extremes, as shown in FIG. 3C.

The interface device can be fabricated, for example, by using 3-D printing of a polymer material. After printing, the parts can be infiltrated with a plastic material to increase the strength and/or rigidity thereof. However, fabrication of the interface device is not limited to the above disclosed techniques. Other fabrication techniques and methodologies are also possible according to one or more contemplated embodiments. For example, the interface device may be machined from a block material or molded.

The translating rings thus provide a way to adjust the fiber positioning to each patient without sacrificing the precise geometric information necessary to create accurate meshes with respect to each source-detector location. Each ring's location can be recorded and a new mesh can be created for each patient based on the location of each ring. A position detector can be provided for each ring to determine the exact location of each ring and thereby the location of the input/output apertures contained thereon. Such position information can be used to reposition the rings and apertures in substantially the same respective positions for subsequent imaging. Such precise positioning may be especially useful for therapy monitoring applications where location of the sources and detectors are carefully maintained across longitudinal imaging time points.

Referring to FIG. 4, a system 402 for imaging of a patient is shown. The system 402 includes the translating ring interface 150 described above. As the interface 150 is designed for optimal patient comfort, a number of adjustable features can be provided. For example, mount 408 can support the imaging interface 150 thereon and can allow for multi-dimension adjustment. For example, the separation between the left and right breast can be changed, as can the height of the breast ring structures. In addition, the mount 408 can provide multiple degrees of freedom for aligning the interface 150 with the patient's breasts independent of the independent translation of the annular members within the interface 150. For example, mount 408 can be similar to a camera mounts with three-dimensional position capability. In addition, a position detector can be provided so as to record the exact location of the interface. Thus, in longitudinal studies, precise positioning can be maintained across imaging time points.

Figures 5A, 5B, 5C:
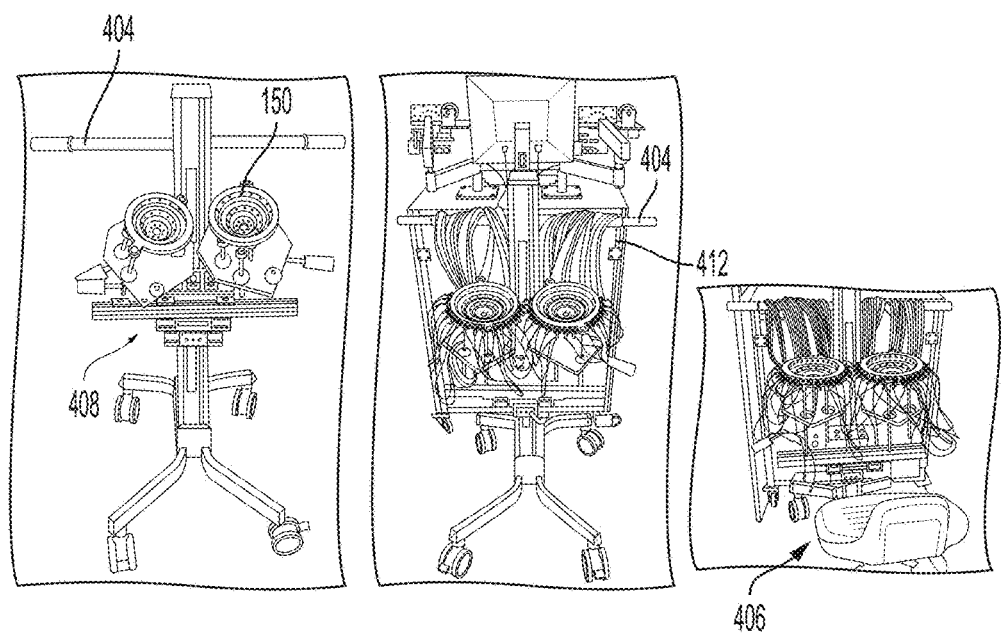
FIG. 5A is an image of a breast screening setup with a translating ring interface prior to connection of optical fibers, according to one or more embodiments of the disclosed subject matter.
FIGS. 5B-5C are images of the breast screening setup of FIG. 5A after connection of optical fibers, according to one or more embodiments of the disclosed subject matter.

For example, the patient can sit in a chair or stool 406 and lean over the interface device 150 to position the breasts within the inner region of the interface device 150. Gravity may serve to assist the positioning of the breast within the interface for imaging purposes, for example, by pulling the breast away from the chest of the patient. Accommodations may be provided to minimize the stress on the patient during imaging. For example, handlebars 404 can be provided for the patient to hold. Handlebars 404 may also serve as a strain release for optical fibers 414, which direct input/output light between the interface 150 and computer 410. In addition, a head rest (not shown), such as a foam head rest, where the patient can rest her chin and/or forehead can also be provided. A user can interact with control unit 410 to affect imaging of the patient by illuminating with input unit 102 and detecting light from the breasts via detection unit 104. Control unit 410 may be configured to process the detected light signals, for example, via detection unit 104 and/or terminal 106 to generate an image of the breast, for example, for viewing on display 412, as described further below. FIGS. 5A-5C show images of a constructed imaging system.

Figure 6:
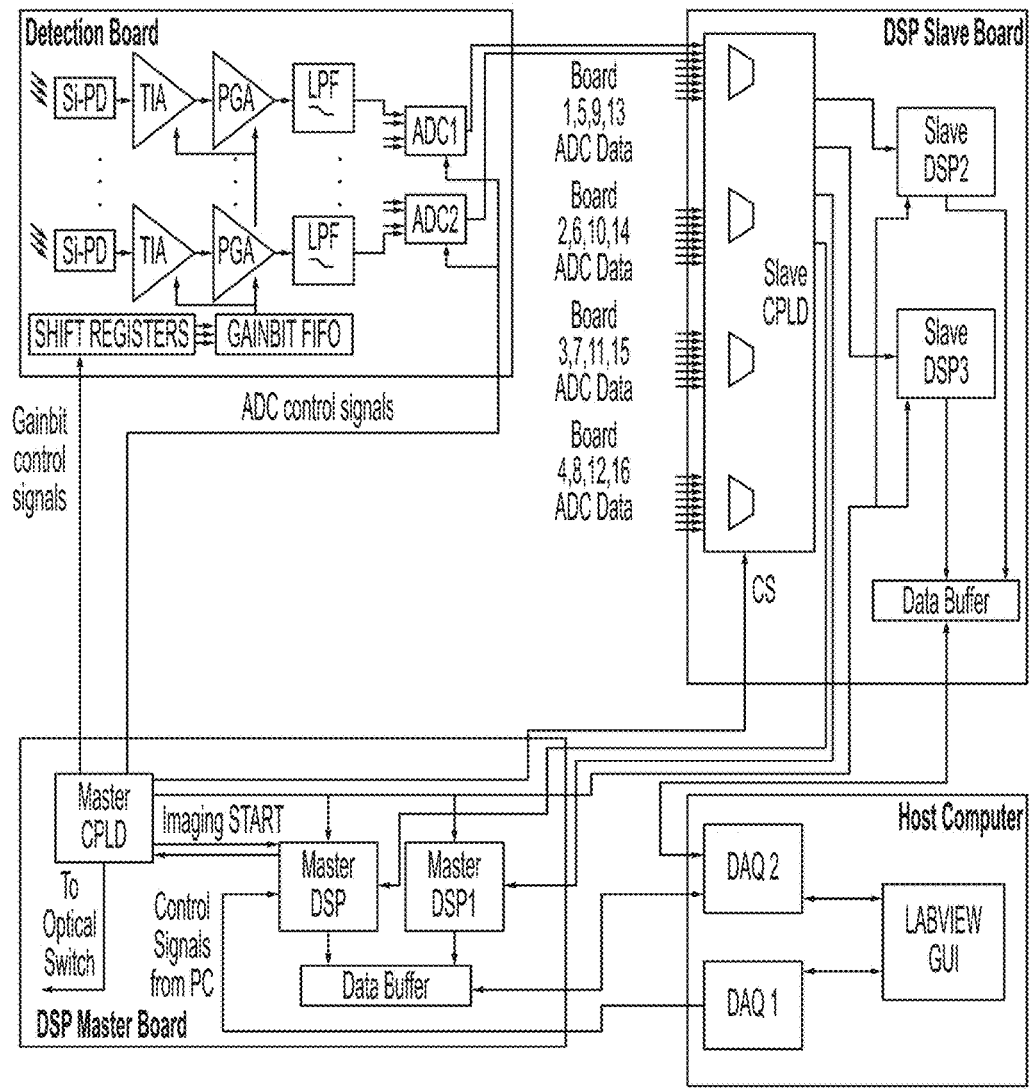
FIG. 6 is a schematic diagram of the detection circuitry and logic for the DOT system, according to one or more embodiments of the disclosed subject matter.

Referring to FIGS. 1 and 6, the light detection unit 104 allows for the fast collection and processing of large amounts of data. An overview of the interactions between the various boards and chips that make up the detection unit 104 is shown in FIG. 6. The detection unit 104 has analog circuitry that amplifies and filters the signal prior to quantization with an analog-to-digital converter 126 (ADC). The ADC 126 interacts with a complex programmable logic device (CPLD) and digital signal processor (DSP) chip at 128 that work to acquire the signal, demodulate the signal to extract the amplitude, and pass the amplitude onto the host computer 106 via data acquisition cards 140, 142. The DSP and CPLD chips also coordinate the timing of the system and keep the various components synchronized while optimizing the system performance.

The analog portion of the detection unit 104 involves converting the detected photons into an electronic signal and then conditioning that signal in preparation for digitization. A plurality of detector boards 116$_n$ can be provided, corresponding to the number of light outputs desired to be simultaneously detected. Each detector board 116$_n$ can include analog electronics with a semiconductor photodetector 118, for example, a silicon photodiode (Si-PD), that converts the incident photons into a current. The current can then be amplified and output as a voltage using a transimpedance amplifier 120 (TIA). The TIA 120 can use a bandwidth extension technique to enable high gain and sufficient bandwidth for the 5 kHz and 7 kHz signals to be amplified. Following the TIA 120, a passive RC high pass filter can remove the DC component of the signal. From there the signal can pass through a second gain stage referred to as the programmable gain amplifier 124 (PGA) that provides additional amplification, but no additional signal to noise ratio (SNR). The PGA is primarily responsible for bringing the signal into a suitable range for detection with the ADC 126.

TABLE 1

Description of the Detection Gain Settings

| Gain Setting | Overall Gain (V/A) | TIA Gain (V/A) | PGA Gain (V/V) |
|---|---|---|---|
| 1 | 10k | 10k | 1 |
| 2 | 100k | 10k | 10 |
| 3 | 1M | 10k | 100 |
| 4 | 10M | 10M | 1 |
| 5 | 100M | 10M | 10 |
| 6 | 1G | 10M | 100 |
| 7 | 10G | 100M | 100 |

In order to control the resistor values across the TIA 120 and the PGA 122 gain stages, three bits can be used to encode a range of gain settings. The resistor values for the TIA 120 range from 10 kΩ to 100 MΩ and the PGA 122 gain ranges from 1 to 100. The three gain bits control the resistor value for the TIA 120 and PGA 122 via a multiplexer and reed relays that are used to switch between the values. The available gain bits and their TIA and PGA gains are shown in Table 1 above.

The gain bits can be controlled through the host computer user interface manually or through an automatic detection routine that will test and select the optimal settings. The optimal setting is determined as the best signal to noise ratio (SNR) without saturation. The obtained gain signals can be used as feedback to determine if adequate contact has been achieved. If this gain value is higher than anticipated, this may indicate insufficient or improper contact. The ring of the interface may be further translated into contact with the breast (e.g., during test illumination and detection) until a gain value closer to an expected value (e.g., indicative of a suitable contact with the tissue surface) is attained. The optical feedback signal may be used for feedback control of the actuator of the embodiment of FIG. 14 for example. In alternative embodiments, a gain value may be determined based on the quality of a signal from a particular detector or each detector in turn. The quality may be determined by comparison to an a priori known reference range or it may be determined by comparing to signals from neighboring detectors. Another indicator of whether a particular level of contact has been achieved is for the system to observe the gain or detector signal as the detector is moved toward the target tissue until a signature is indicated, for example, an abrupt change in gain.

The host computer passes the gain bits to the DSP through a series of shift registers that daisy-chain through the detection boards. Once all of the gain bits have been chained through the boards 116$_n$, a signal transfers the gain bits into a first-in-first-out (FIFO) buffer for storage on each detection board. During imaging, as the source position is changed, the new gain bit settings are read out locally from the FIFO thereby quickly modifying the resistor values across the TIA 120 and PGA 122.

Following the TIA 120 and PGA 122 gain stages, the signal is filtered with an 8th order Butterworth anti-aliasing filter that removes high frequency components and whose primary purpose is to ensure there are no frequencies present above the Nyquist frequency prior to digitization. The signal can be sampled at 75 ksamples/s, which means that the Nyquist frequency is 37.5 kHz. As a result, a cutoff frequency of 12.5 kHz can be chosen. The Butterworth filter can have a flat passband for the 5 and 7 kHz signals, while also providing strong attenuation of any higher frequency noise at risk of aliasing into the passband. Finally, an operational amplifier offsets the signal so that it is centered around 2.5 V in order to take advantage of the full 0-5 V input range of the ADC 126.

Finally the signal is brought into the digital domain using a four channel, 16-bit, successive approximation register (SAR) ADC 126 that samples at a maximum rate of 1 Msamples/s. The ADC 126 can sample the data from each detector channel at 75 kHz. The ADC timing can be synchronized with the rest of the digital electronics through the master CPLD 126 and DSP 132.

This DSP-based system utilizes a master-slave architecture for expanding the data acquisition capabilities to multiple DSP chips as opposed to a single DSP chip. Such a design accommodates an increased number of sources, detectors, and wavelengths for breast imaging. The master DSP (mDSP) chip 132 is the single DSP that coordinates the behavior of the system, including the other slave DSP (sDSP) chips 130a-130c. It handles all of the handshaking with the host computer and works with the master CPLD (mCPLD) 136 to control the timing of the optical switch, gain bits, and acquisition of the signals from the ADCs 126. The mDSP 132 can rely on the mCPLD 136 to control the timing of all of the signals related to shifting and setting the gain bits, controlling the conversion and sampling from the ADCs 126, and sending out the address signals to control the source position of the optical switch.

The mDSP 132 and mCPLD 136 work closely together to control the timing of the events in the system and to communicate with the other chips. The mCPLD 136 is used to communicate the control logic to the detection boards, but the mDSP 132 closely controls the mCPLD 136 and is responsible for timing the 7 ms for the optical switch settling. The intricate way in which the mDSP 132 and mCPLD 136 work together to progress through the various states of setup and acquisition is shown in Table 2.

The mDSP 132 also relies on a slave CPLD 134 (sCPLD) whose job is to multiplex the incoming data from the detector ADC chips 126 (each responsible for digitizing 4 detector channels) and routing it to the DSP chips for processing. This multiplexing is controlled through a chip select (CS) signal that keeps the CPLDs, ADCs, and DSPs in sync. Each DSP acquires two simultaneous serial streams of data through the A and B serial ports. One DSP is referred to herein as the master DSP 132 (mDSP) because it is in charge of the system, while the other three DSP chips 130a-130c (sDSP1, sDSP2, sDSP3) are referred to as slave chips because they can only respond to one signal (e.g., IMAGING Start) that tells them to either acquire data or sit idly. The master-slave configuration helps simplify the control of the system and keeps the data acquisition for all DSP chips in unison. This configuration also allows for easy scaling of the system for a larger number of sources, wavelengths, or detectors which is achieved either by reprogramming the existing DSPs or by adding additional slave DSP chips.

TABLE 2

State by State Description of the PC, mCPLD, and mDSP Interaction

| State | Description |
|---|---|
| Standby | mDSP is idle waiting for a signal from the host computer. mCPLD is idle waiting for a signal from the mDSP. |
| System Parameters | 1. mDSP receives CMD:01 from the host computer telling it to go into the System Parameters state.<br>2. The host computer sends the number of sources, detectors, and wavelengths to the mDSP. |

TABLE 2-continued

State by State Description of the PC, mCPLD, and mDSP Interaction

| State | Description |
|---|---|
| | 3. mDSP returns to Standby.<br>*mCPLD remains in Standby. |
| Gain Bit | 1. mDSP receives CMD:10 from the host computer telling it to go into the Gain Bit download state.<br>2. PC sends the gain bits for each source-detector pair.<br>3. mDSP tells the mCPLD to go into Gain Bit state.<br>4. mDSP sends the mCPLD the # of sources, detectors, wavelengths.<br>5. mDSP sends the gain bits through the mCPLD to the detection boards while the mCPLD sends out control signals to the Gain Bit Shift Registers and FIFOs.<br>6. mDSP and mCPLD return to Standby. |
| Imaging | 1. mDSP receives CMD:11 from the host computer telling it to acquire one frame.<br>2. mDSP tells mCPLD to go into Imaging State.<br>3. mCPLD tells the optical switch to move to the next position. Updates the gain bits by reading from the detection board FIFOs. Waits for the TIMER signal from mDSP.<br>4. DSP counts to 7 ms and then signals TIMER to mCPLD. During that time it also runs the lock-in detection and sends data from previous source back to the PC.<br>5. mCPLD acquires 150 samples from all detectors.<br>6. mDSP receives data from the ADC. Returns to step 3 until all sources and wavelength sets are acquired.<br>7. mDSP and mCPLD return to Standby. |

Each pair of DSP chips (mDSP 132 with sDSP1 130a; sDSP2 130b with sDSP3 130c) can share an 8,192×9 dual synchronous FIFO data buffer 138, through which the data is sent back to the host computer 106. The DSP chips can write to the FIFO 138, which modifies the 'EMPTY' signal of the FIFO, thereby triggering a request to the host computer 106. The host computer 106 then grants the request and triggers a read to the FIFO 138, which sends the data to a user interface 144. As a result, the FIFO 138 is essentially a data buffer that is responsible for holding the data until the host computer is ready. The control signals from the user interface are passed to the detector hardware through a data acquisition card 142, for example, a 24 bit digital I/O interface. The data from the DSP chips is acquired by the host computer 106 through a data acquisition card 140, for example, providing 32 digital data lines that are individually configurable as input or output, grouped into four 8-bit ports. Each group of 8-bit ports can be devoted to one DSP in order to handle the data transfer to the host computer.

Each DSP can be responsible for demodulating the incoming data to extract the amplitude of the signal. A digital lock-in detection algorithm can be employed. For example, the algorithm can use a simple averaging filter to extract the amplitude of the signal based on a specific relationship between $f_m$, the frequency of the signal (7 kHz and 5 kHz in this system), and $N_s$, the number of samples acquired, as shown in:

$$f_m = \frac{kf_s}{N_s}, 1 \le k \le \frac{N_s}{2} \tag{1}$$

Performing the lock-in detection digitally using a DSP chip as opposed to using traditional analog circuitry not only reduces the amount of hardware required for demodulation, but also provides a more robust solution with better noise performance. Simply by reprogramming the DSP chip it is possible to adjust the lock-in frequency, filtering, and the number of detectors. In addition, DSP-based demodulation is less sensitive to analog component tolerances that can vary with temperature and age as well as between detector channels. To obtain fast imaging speeds, careful coordination between the various components of the system, may be necessary while also accounting for the settling times of the electronics and optical switch. There are many occasions where the system multi-tasks to optimize the imaging speed. The system timing is outlined in detail in FIG. 7.

For example, the DSPs can acquire 150 samples from each of 128 detectors over a period of 2 ms so that each detector is effectively sampled at 75 ksamples/s. The chip select signal (CS) sequentially selects two ADCs per DSP at a time to pass the digitized samples onto that DSP. Each 16-bit ADC can digitize two channels at a time and passes them onto the DSP as one 32-bit packet. For example, mDSP first receives sample 1 from channels 1&3 of ADCs 1&2, followed by sample 1 from channels 1&3 of ADCs 3&4, followed by sample 1 from channels 1&3 of ADCs 5&6, and finally sample 1 from channels 1&3 of ADCs 7&8. It then proceeds to acquire sample 1 from channels 2&4 from each set of ADCs before moving onto the next sample. In parallel, sDSP1, sDSP2, and sDSP3 are receiving data from ADCs 9 through 32. The sCPLD is responsible for coordinating the routing of the ADC data to the appropriate DSP in each cycle, as coordinated by the chip select (CS) signal. Once the DSPs have received 150 samples from all 128 detectors, the mDSP signals to the mCPLD to change the source position and begins the 7 ms pause waiting for the switch to settle. During that settling time the speed of the system is optimized by having the DSPs run the lock-in detection on the samples from the previous source before sending them out to the host computer. In addition, while the optical switch is settling on the new source position, the gain bits are updated, and the analog electronics have time to settle.

This system was designed for dynamic breast imaging, making the dynamic range and the speed of acquisition two of the primary criteria. The temporal response is limited by the settling time of the optical switch and the number of source positions and wavelengths. The switch requires 7 ms to settle after switching positions, followed by 2 ms to acquire the data for all detectors at that source position. This brings the imaging time to 9 ms per source position. Since two wavelength sets are sequentially imaged, the imaging rate also depends on the number of wavelengths. Consequently the fastest the system can image is to collect one frame in 0.009 seconds with one source and 2 wavelengths (e.g., 111 Hz). Or, with 32 sources and 2 wavelengths it can acquire a frame in 0.288 seconds (e.g., 3.5 Hz). Finally, the slowest configuration is to use all 32 sources and 4 wavelengths in which case it takes 0.576 seconds to acquire one frame (e.g., 1.7 Hz).

Three dimensional reconstructions are performed for the measurement data by using a PDE-constrained multispectral imaging method. A brief description of this method, including the diffusion approximation as a light propagation model and the PDE-constrained inverse model of directly recovering chromophore concentrations in tissue, is provide below.

Light propagation in scattering-dominant media such as breast tissue is well described by the diffusion approximation (DA) to the equation of radiative transfer as:

$$-\nabla \cdot D(\vec{r})\nabla u(\vec{r}) + \mu_a u(\vec{r}) = \quad (2)$$

$$f(\vec{r}) \text{ in } X \text{ s.t. } u(\vec{r}) + 2D(\vec{r})A\frac{\partial u(\vec{r})}{\partial \vec{n}} = 0 \text{ in } \partial X,$$

where A is related to reflection due to mismatched refractive indices, $u(\vec{r})$ is the radiation density, and $D(\vec{r})$ is the diffusion coefficient given by:

$$D = \frac{1}{3(\mu_a + \mu_s')}.$$

The solution to (2) provides a prediction of the measurement at the medium surface:

$$P_\lambda = Qu_\lambda$$

where Q represents a measurement operator that projects the forward solution $u(\vec{r})$ onto the measurable quantity by our digital dynamic imaging system. The basic idea behind DOT imaging of tissue chromophores is to exploit the linear correlation between the tissue absorption and the concentrations of chromophores in tissue as:

$$\mu_a(\lambda) = \Sigma_{i=1}^{N_C} \varepsilon_i(\lambda) C_i, \quad (3)$$

where $\varepsilon_i(\lambda)$ and $C_i$ are the absorption extinction coefficient and the concentration, respectively, for the i-th chromophore in tissue, and $N_C$ is the number of total chromophores that contribute to the absorption at wavelength $\lambda$. The major chromophores relevant to breast imaging are oxygenated hemoglobin ($HbO_2$), deoxygenated hemoglobin (Hb), water ($H_2O$) and lipid, whose molar extinction coefficients are well documented in the literature. The multi-spectral inverse model can directly recover the spatial distributions of chromophore concentrations by using data from all wavelengths simultaneously during the reconstruction. This is achieved here with the following Lagrangian formulation for PDE-constrained multispectral optimization:

$$L(x, u_\lambda; \eta_\lambda) = \frac{1}{2}\sum_\lambda |Qu_\lambda - z_\lambda^{obs}|^2 + \beta R + \sum_\lambda \eta_\lambda^T(Au_\lambda - b). \quad (4)$$

Here x is a vector of all unknown chromophores that may include $HbO_2$, Hb, $H_2O$, or lipid concentrations, Au=b is a system of discretized diffusion equations, $z_\lambda$ is the measurement at wavelength $\lambda$, and $\beta$ is a regularization parameter that controls a strength of smoothing R.

A radial basis function (RBF)-type smoothing operator can be used, since it performs better on a grid of unstructured meshes. The PDE-constrained multispectral inverse problem can be solved within a framework of the reduced Hessian sequential quadratic programming method (rSQP) that accelerates the reconstruction process. The rSQP method finds the next step $p=(\Delta x, \Delta u)$ through the minimization to a quadratic approximation of the Lagrangian function L subject to the linearized constraints:

$$\min \Delta x^{kt} g_r^k + \frac{1}{2}\Delta x^{kT} H_r^k \Delta x^k \quad (5)$$

$$\text{subject to } C^k \Delta p^k + (Au_\lambda - b)^k = 0,$$

where $g^k$ is the reduced gradient and $H_r^k$ is the reduced Hessian of the Lagrangian function. Here $C^k$ denotes the Jacobian matrix of the DA with respect to $p=(x,u)$ and is given by:

$$C^k = (Au_\lambda - b)_p^{kT}.$$

With the solutions of the quadratic problem (5), the new iterates can be obtained for both the forward and inverse variables in each step of optimization as:

$$x^{k+1} = x^k + \alpha^k \Delta x^k$$

$$u_\lambda^{k+1} = u_\lambda^k + \alpha^k \Delta u_\lambda^k \quad (6)$$

where $\alpha^k$ is the step length chosen through a line search. The reduced-space formulation is described in detail in "A PDE-constrained SQP algorithm for optical tomography based on the frequency-domain equation of radiative transfer," published in 2009 in volume 25, number 1 of the journal *Inverse Problems*, which is hereby incorporated by reference herein in its entirety. The method described above can be used to reconstruct chromophores concentrations in breast tissue, as shown, for example in FIG. 8, which shows static optical images of sagittal slices of a tumor bearing breast over time during a cancer treatment obtained using the disclosed optical imaging system.

According to embodiments of the disclosed subject matter, the translating ring interface can include various features designed to provide intimate contact between the input/output apertures of the annular members and the breast surface while avoiding (or at least reducing) uncomfortable compression of the breast tissue. For example, radially inner portions having the input/output apertures thereon can be configured to be displaced in a radial direction of the annular members so as to accommodate various breast sizes and shapes. Such an interface is shown in FIGS. 9A-9B. The interface includes a plurality of annular members 902a-902e, each with a respective radially inner portion 904 that has an inner surface 906 bounding an inner region of the interface. The breast 108 is inserted into the inner region of the interface, but one or more of the annular members may not contact the surface 908 of the breast 108 once it is fully inserted into the interface, as shown in FIG. 9A. Each annular member 902a-902e includes an actuator 910, for example, a linear actuator, that moves the inner portion 904 in a radial direction so as to contact the inner surface of each annular member 902 with the breast surface 908.

The quality of contact made between the breast and the annular member can be computed based on the amplitude and characteristics of the light detected back from the sensors in the annular member. For example, when no contact is made, an air layer may exist between the light source and the tissue that results in high air-tissue light reflections. These light reflections can cause detected signals from sensors close to the light source that are much larger than expected while detected signals from sensors farther from the light source (e.g., on an opposite side of the breast from the light source aperture) are much lower than expected. A closed loop control system can use these detected signals to control the positioning of each annular member for optimal contact. Alternatively or additionally, the control system can employ pressure sensors, proximity sensors, optical sensors, or acoustic sensors to characterize the contact between the tissue and the annular member in order to optimize the contact.

In another example, radially inner portions can be configured to be displaced by insertion of the breast tissue into the interface, as shown in FIGS. 10A-10B. The interface includes a plurality of annular members 1002a-1002e, each with a respective radially inner portion 1004 that has an inner surface 1006 bounding an inner region of the interface. The inner portions 1004 can be mounted on flexures 1010, for example, helical springs, that allow motion in the radial direction. At least initially, the inner portions 1004 can define an inner region that is too small to accommodate the size of breast 108, as shown in FIG. 10A. However, as the breast in inserted into the inner region, flexures 1010 allow motion of the inner portions 1004 in a radially outer direction, thereby keeping the inner surfaces 1006 in intimate contact with the breast surface 1008 with minimal compression of the breast tissue, as shown in FIG. 10B. In addition, the flexures 1010 may allow rotation of the inner portion 1004 out of the plane of the particular annular member to allow alignment of the inner surface 1006 with the breast surface 1008, thereby further avoiding patient discomfort.

In order to precisely characterize the location of each inner portion 1004, one or more sensors 1012 can be provided. The sensors 1012 can be electromagnetic, optical, or any other sensing capable of providing a measure of displacement of the radially inner portion 1004. For example, sensor 1012 can determine the force exerted on flexure 1010, which relates to a displacement of the flexure 1010 and the portion 1004. In another example, flexure 1010 may include multiple flexures supporting each inner portion 1004. Sensor 1012 for each of the multiple flexures can then be used to determine a radial displacement of the inner portion 1004 as well as an out of plane displacement (e.g., out of plane rotation). For example, a difference in forces between the multiple flexures may correspond to an amount of rotation of the inner portion 1004, which can be used to precisely determine a location of the inner portion 1004.

In still another example, radially inner portions can be formed of a deformable material so as to conform to breast tissue inserted into the interface, as shown in FIGS. 11A-11B. The interface includes a plurality of annular members 1102a-1102e, each with a respective radially inner portion 1104 formed of a deformable material. For example, the deformable material may be a flexible polymer, gel-filled bladder, liquid-filled bladder, or air-filled bladder. At least initially, the inner portions 1104 can define an inner region that is too small to accommodate the size of breast 108, as shown in FIG. 11A. However, as the breast is inserted into the inner region, the interaction between the breast surface 1108 and the inner portion 1104 causes the inner portion 1104 to conform to the breast surface 1108, as shown in FIG. 11B. The apertures may be arranged on the inner portion 1104 such that after an expected compression the input/output is substantially perpendicular to the breast surface 1108. The ultimate shape of the deformable material 1104 after alteration by the breast insertion can be quantified in order to generate a mesh using optical techniques.

Figure 12A:
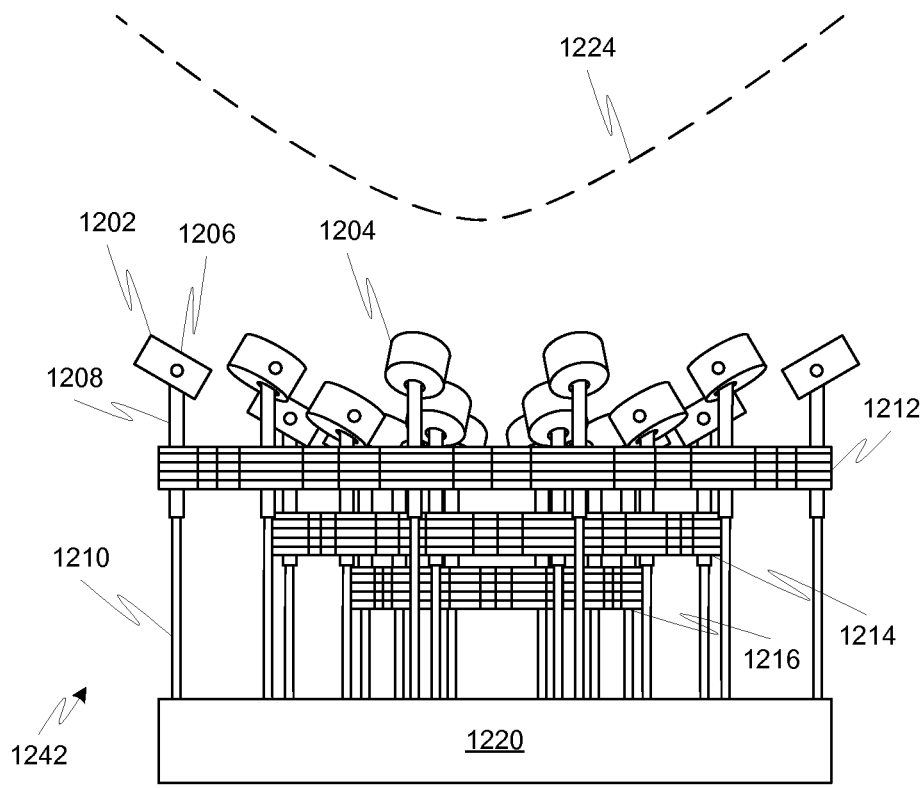
FIGS. 12A and 12B illustrate another embodiment of a translating ring interface adjustable supports for optical elements according to embodiments of the disclosed subject matter.
Figure 12B:
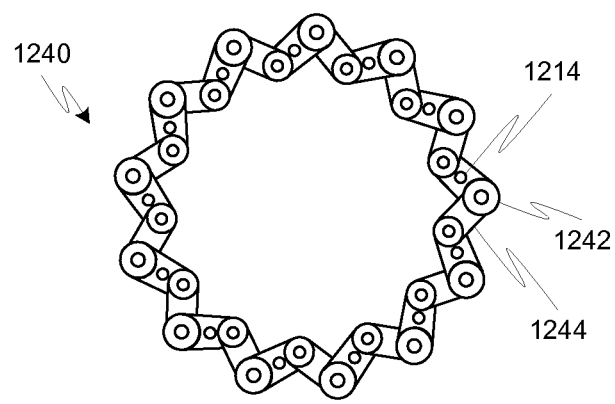

FIGS. 12A and 12B illustrate an embodiment in which optical elements 1202 and 1204 are indirectly attached to annular elements 1212, 1214, and 1216 by cylinders 1208 that can slide on stems 1210 that rise from and are supported by a base 1220. The optical elements 1202 and 1204 (only two are labeled to avoid making the drawing too busy) are adjustable in groups by translating each annular element 1212, 1214, and/or 1216 up or down on the stems 1210. As a result, each of the optical elements 1202 and 1204 belongs to a ring shaped array of optical elements that can be positioned to define a bounding surface 1224 in the shape of a body part, such as a breast, to be interrogated. The head of each stem can be articulated in order to make sufficient angular contact orthogonal to the tissue surface. An additional mode of customization of the arrangement of the optical elements may be provided by making expandable or reshapable annular elements as illustrated in FIG. 12B. Annular member 1240 may be made such that its overall diameter (and in embodiments, it shape as well) can be increased or reduced, thereby changing the radial separation of the optical elements as well as their axial position. In the illustrated embodiment, the cylinders 1208 are held in openings 1214 in links 1244 connected by hinges 1242 which pivot with sufficient friction to hold an imposed shape and size.

Although specific examples have been described above with sources and detectors located remote from the interface and coupled to respective apertures via optical fibers, embodiments of the disclosed subject matter are not limited thereto. Rather, the source and/or the detectors can be directly embodied in the individual members of the interface. For example, each interface member can include a multiplicity of sources, for example laser diodes, and a multiplicity of detectors, for example photodiodes, at the location of the apertures. Appropriate illumination/detection electronics can be included with each member. Detected data can be conveyed to a central processor, for example, via wireless or wired transfer, for image processing.

While specific examples of interfaces with ring-shaped and annular configurations have been discussed herein, embodiments of the disclosed subject matter are not limited thereto. Rather, other shapes and configurations allowing for conformal touch contact with the patient body part while providing repeatable, detectable source/detector positions are also contemplated.

For example, multiple piece-wise continuous members can be used to form each annular section. In another example, the input/output members of the interface may form a C-shaped, oval, rectangular, or any other shape, so long as the inputs and outputs can be brought into conformal, substantially non-compressive contact with the imaging tissue. Alternatively or additionally, the input/output members may selectively apply compressive forces to the tissue as part of diagnostic imaging, for example, to determine dynamic vascular response based on the pressure exerted by the input/output members.

For example, FIG. 13 shows a schematic of a generalized interface for tissue imaging. An interface member 1302 can include an optical input and/or output 1304, such as a laser diode and/or photodiode. Alternatively, the optical inputs/outputs 1304 can be apertures connected to remote sources and detectors by optical waveguides, as described above. For example, each member may have a single optical input and/or a single optical output. Moreover, the system may include a plurality of individual members. Each member 1302 can be independently positionable in contact with the tissue surface irrespective of other members 1302 associated with the system. A contact determination device 1306 can be provided for detecting when the member 1302 is in contact with the tissue. A controller 1312 can use the information provided by the contact determination device 1306 to move the member 1302 into contact with the tissue using actuator 1308. The actuator 1308 may be capable of moving the member 1302 in multiple directions, for example, in at least two dimensions, as well as rotationally so as to position an interrogation/detection surface of the member 1302 into conformal contact with the tissue surface. Processor 1310 can use position information of the member 1302 provided by controller 1312 based on the actuation in constructing the imaging mesh. Each member 1302 can represent a particular point of the imaging mesh, with each member 1302 being positioned at a desired mesh position (e.g., with respect to prior imaging sessions). The imaging interface with a plurality of interface members 1302 can thus conform to a variety of tissue geometries and shapes without necessarily being constrained to a ring or annular geometry.

FIG. 14 shows an actuator 1262 configured to move a probe head 1264 such that it makes suitable contact with a body part surface 1266 or such that the probe head 1264 applies pressure to and removes pressure from the body part in order to induce a change in the tissue that is contemporaneously interrogated. For example, the force of the actuator may be used to push blood away from the site and then the release or reduction of that force may allow blood to flow back. During the motion of the actuator 1262, successive image frames or other data may be captured to allow instantaneous or time-averaged indications of the concentration and location of chromophores. The imaging system connected to the probe can also be used for determining whether contact is made or not. Various control goals may be used for governing the actuation of the probe head.

In any of the embodiments, the mesh for imaging can be generated based on encoder values for each of the source/detector positions, e.g., based on the positions of the annular member. In addition, the optimal position of each annular member and/or the source/detector positions therein can be estimated or predicted based on previously obtained information regarding the tissue or the patient. For example, information regarding patient weight, height, age, body-mass index, bra size, and/or images of the patient (e.g., MRI, CT, PET, or optical images) can be used to determine an optimal initial configuration of the imaging setup, including, but not limited to, patient chair height, interface height and tilt, initial interface member arrangement, number of interface members, etc. Fine tuning to provide contact of the imaging interface with the patient tissue can be accomplished via feedback controlled actuation.

Embodiments of the disclosed subject matter thus avoid issues associated with other breast imaging interfaces, namely, incomplete breast coverage, the inability to image a range of breast sizes (A to DDD), the use of matching fluid, the use of compression, the inability to extract the precise optical input/output positioning.

It will be appreciated that the methods, processes, and systems described above can be implemented in hardware, hardware programmed by software, software instruction stored on a non-transitory computer readable medium or a combination of the above. For example, the processors described herein can be configured to execute a sequence of programmed instructions stored on a non-transitory computer readable medium. The processors can include, but are not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, or another structured or object-oriented programming language. The sequence of programmed instructions and data associated therewith can be stored in a non-transitory computer-readable medium such as a computer memory or storage device which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

Furthermore, the disclosed methods, processes, systems, and/or algorithms can be implemented by a single processor or by a distributed processor. Further, it should be appreciated that the steps discussed herein can be performed on a single or distributed processor (single and/or multi-core). Also, the methods, processes, systems, and/or algorithms described in the various figures of and for embodiments above can be distributed across multiple computers or systems or can be co-located in a single processor or system. Exemplary structural embodiment alternatives suitable for implementing the methods, processes, systems, and/or algorithms described herein are provided below, but not limited thereto.

The methods, processes, systems, and/or algorithms described herein can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example. Moreover, embodiments of the disclosed methods, processes, systems, and/or algorithms (i.e., computer program product) can be implemented in software executed on a programmed general purpose computer, a special purpose computer, a microprocessor, or the like.

Embodiments of the disclosed methods, processes, systems, and/or algorithms (or their sub-components or modules), can be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, etc. In general, any process capable of implementing the functions or steps described herein can be used to implement embodiments of the methods, processes, systems, algorithms and/or computer program product (software program stored on a non-transitory computer readable medium).

Furthermore, embodiments of the disclosed methods, processes, systems, and/or algorithms can be readily implemented, fully or partially, in software using, for example, object or object-oriented software development environments that provide portable source code that can be used on a variety of computer platforms. Alternatively, embodiments of the disclosed methods, processes, systems, and/or algorithms can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the disclosed methods, processes, systems, and/or algorithms can be implemented in hardware and/or software using any known or later developed systems or structures, devices and/or software by those of ordinary skill in the applicable art from the function description provided herein and with a general basic knowledge of imaging and/or computer programming arts.

Furthermore, the foregoing descriptions apply, in some cases, to examples generated in a laboratory, but these examples can be extended to production techniques. For example, where quantities and techniques apply to the laboratory examples, they should not be understood as limiting. In addition, although specific chemicals and materials have been disclosed herein, other chemicals and materials may also be employed according to one or more contemplated embodiments.

Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, interfacing systems, devices, and methods for optical imaging. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. An interfacing device for optical tomographic imaging of breast tissue, the interfacing device comprising:
    a plurality of annular members concentrically arranged in a stacked configuration along an axial direction forming a stack,
    each annular member of the plurality of annular members being a monolithic piece having an inner surface facing toward the breast tissue and arranged to contact the breast tissue when the interfacing device is in use,
    the inner surface of each annular member having an inner diameter that is different from inner diameters of the other annular members and the inner surface coming into contact with the breast tissue when the interfacing device is in use,
    the plurality of annular members being arranged such that their respective inner diameters increase from a first axial end of the stack to an opposite second axial end of the stack,
    each of the annular members including a plurality of optical input apertures and optical output apertures on its inner surface, wherein the inner surface is monolithic except for the apertures on the inner surface,
    the stack forming an inner region bounded by the inner surfaces of the annular members for receiving the breast tissue for imaging, wherein
    the interfacing device further includes a translation device connected to each annular member for displacing each annular member along the axial direction so as to adjust spacing between adjacent annular members in said stack.

2. The interfacing device of claim 1, wherein the optical input apertures and optical output apertures are alternately arranged equidistantly around a circumference of the inner surface of each annular member.

3. The interfacing device of claim 1, wherein the inner surface of each annular member is arranged at an angle with respect to the axial direction of the stack, the angle for each annular member being different from that of the other annular members.

4. The interfacing device of claim 1, wherein the annular members include a plurality of optical fiber connections corresponding to each of the optical input apertures and the optical output apertures.

5. The interfacing device of claim 4, wherein angles of the optical fiber connections for the annular members with respect to the axial direction increase from the first axial end of the stack to the second axial end of the stack.

6. The interfacing device of claim 5, wherein the plurality of annular members is four annular members, the angle of the optical fiber connection for a first annular member at the first axial end of the stack is 30°, the angle of the optical fiber connection for a second annular member adjacent to the first annular member is 45°, the angle of the optical fiber connection for a third annular member adjacent to the second annular member is 60°, and the angle of the optical fiber connection for a fourth annular member at the second axial end of the stack is 75°.

7. The interfacing device of claim 1, wherein
the plurality of annular members is five annular members,
a first annular member at the first axial end of the stack includes eight apertures,
a second annular member adjacent to the first annular member includes twelve apertures,
a third annular member adjacent to the second annular member includes twelve apertures,
a fourth annular member adjacent to the third annular member includes sixteen apertures, and
a fifth annular member at the second axial end of the stack includes sixteen apertures.

8. The interfacing device of claim 1, further comprising a plurality of multimode optical fibers connected to the plurality of optical input and optical output apertures.

9. The interfacing device of claim 1, further comprising a controller for controlling the translation device and at least one contact sensor,
wherein the translation device includes a spring plunger, a stepper motor, or a linear actuator,
the at least one contact sensor is a pressure, temperature, optical, or acoustic sensor configured to provide an indication of contact of a surface of one of the annular members with the breast tissue, and
the controller is configured to control displacement of each annular member responsively to a signal from the at least one contact sensor.

10. The interfacing device of claim 1, further comprising a mount for supporting the stack of annular members thereon, the mount being configured to allow three-dimensional positioning of the stack with respect to the breast tissue.

11. The interfacing device of claim 1, further comprising position sensors that indicate a position of each annular member.

12. The interfacing device of claim 1, wherein each annular member is formed of a polymer material.

13. The interfacing device of claim 1, wherein each annular member is formed of a 3-D printed polymer infiltrated with plastic or an injection molded plastic.

14. A system for optical tomographic imaging of breast tissue, the system comprising:
a translating ring interface including
a plurality of annular members concentrically arranged in a stack along an axial direction with the annular members constructed to be translated with respect to each other along the axial direction so as to adjust spacing between adjacent annular members in the stack,
each annular member of the plurality of annular members being a monolithic piece having an inner surface facing toward the breast tissue and arranged to contact the breast tissue when the translating ring interface is in use,
the inner surface of each annular member having an inner diameter that is different from inner diameters of the other annular members,
the plurality of annular members having respective inner diameters that increase from a first axial end of the stack to an opposite second axial end of the stack,
each of the annular members including a plurality of optical input apertures and optical output apertures on its inner surface, wherein the inner surface is monolithic except for the apertures on the inner surface,
the translating ring interface having an inner region bounded by the inner surfaces of the annular members for receiving the breast tissue, the inner surfaces contacting the breast tissue during imaging;
a translation device connected to each annular member and configured to displace each annular member along the axial direction;
a plurality of illumination sources;
a plurality of first optical fibers connecting the plurality of illumination sources to the optical input apertures;
a plurality of detectors;
a plurality of second optical fibers connecting the plurality of detectors to the optical output apertures; and
a processor configured to control the illumination sources to illuminate the breast tissue with light via one of the first optical fibers and to control the detectors to detect light from the breast tissue via the second optical fibers,
wherein the processor is configured to modulate amplitude of light from the illumination sources during illumination and to demodulate the light detected by the detectors to generate detected light signals.

15. The system of claim 14, wherein the illumination sources are laser diodes that are monochromatic.

16. The system of claim 14, wherein the detectors are silicon photodiodes.

17. The system of claim 14, wherein each of the illumination sources generates light at a wavelength in a near infrared wavelength range different from the other illumination sources.

18. The system of claim 17, wherein each of the illumination sources generates light at a wavelength of 765 nm, 808 nm, 827 nm, or 905 nm.

19. The system of claim 14, wherein the processor is configured to modulate a first pair of the illumination sources at a first frequency and to modulate a second pair of the illumination sources at a second frequency different from the first frequency, and further comprising an optical combiner for combining light from one of the first pair with light from one of the second pair for simultaneously illuminating the breast tissue.

20. The system of claim 14, wherein the processor is configured to reconstruct an image of the breast tissue based on the detected light signals.

21. The system of claim 20, further comprising position sensors that indicate a position of each annular member with respect to the breast tissue, wherein the processor is configured to use the position of each annular member in reconstructing the image of the breast tissue.

22. The system of claim 14, further comprising a mount for supporting the stack of annular members thereon, the mount being configured to allow three-dimensional positioning of the stack with respect to the breast tissue.

* * * * *

UNITED STATES PATENT AND TRADEMARK OFFICE
CERTIFICATE OF CORRECTION

PATENT NO. : 10,376,150 B2
APPLICATION NO. : 14/348072
DATED : August 13, 2019
INVENTOR(S) : Hielscher et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 210 days.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*